United States Patent
Ghezzi et al.

(10) Patent No.: US 9,938,518 B2
(45) Date of Patent: Apr. 10, 2018

(54) ORGANIC DEVICES FOR THE PHOTOINHIBITION OF EXCITABLE CELLS

(71) Applicants: FONDAZIONE ISTITUTO ITALIANO DI TECNOLOGIA, Genoa (IT); ISTITUTO DON CALABRIA—OSPEDALE CLASSIFICATO SACRO CUORE, Verona (IT)

(72) Inventors: Diego Ghezzi, Genoa (IT); Fabio Benfenati, Genoa (IT); Guglielmo Lanzani, Milan (IT); Maria Rosa Antognazza, Venegono Inferiore (IT); Giuliano Freddi, Senago (IT); Ilaria Donelli, Milan (IT); Maurizio Mete, Fano (IT); Grazia Pertile, Negrar (IT)

(73) Assignees: FONDAZIONE ISTITUTO ITALIANO DI TECNOLOGIA, Genova (IT); ISTITUTO DON CALABRIA—OSPEDALE CLASSIFICATO SACRO CUORE, Verona (IT)

( * ) Notice: Subject to any disclaimer, the term of this patent is extended or adjusted under 35 U.S.C. 154(b) by 79 days.

(21) Appl. No.: 14/909,144

(22) PCT Filed: Aug. 1, 2014

(86) PCT No.: PCT/IB2014/063616
§ 371 (c)(1),
(2) Date: Feb. 1, 2016

(87) PCT Pub. No.: WO2015/015464
PCT Pub. Date: Feb. 5, 2015

(65) Prior Publication Data
US 2016/0168561 A1 Jun. 16, 2016

(30) Foreign Application Priority Data
Aug. 2, 2013 (IT) .............................. TO2013A0665

(51) Int. Cl.
*C12N 13/00* (2006.01)
*C08J 7/04* (2006.01)
(Continued)

(52) U.S. Cl.
CPC .............. *C12N 13/00* (2013.01); *C08J 7/045* (2013.01); *C09D 165/00* (2013.01);
(Continued)

(58) Field of Classification Search
CPC ........ C12N 13/00; C12M 23/22; C12M 35/02
See application file for complete search history.

(56) References Cited

U.S. PATENT DOCUMENTS

| | | | |
|---|---|---|---|
| 2010/0255555 A1* | 10/2010 | Lee | ........................ C12N 1/066 435/173.1 |
| 2011/0301529 A1 | 12/2011 | Zhang et al. | |
| 2013/0199601 A1* | 8/2013 | Vardeny | ................. B82Y 10/00 136/255 |

FOREIGN PATENT DOCUMENTS

| | | |
|---|---|---|
| WO | 2007040601 A1 | 4/2007 |
| WO | 2010051343 A1 | 5/2010 |

OTHER PUBLICATIONS

Aleksandra Polosukhina, Jeffrey Litt, Ivan Tochitsky, Joseph Nemargut, Yivgeny Sychev, Ivan De Kouchkovsky, Tracy Huang, Katharine Borges, Dirk Trauner, Russell N. Van Gelder and Richard H. Kramer, Photochemical Restoration of Visual Responses in Blind Mice, Neuron Article, Cell Press, Jul. 26, 2012, pp. 271-282, Neuron 75, Elsevier Inc.
(Continued)

*Primary Examiner* — William H. Beisner
(74) *Attorney, Agent, or Firm* — Robert E. Alderson, Jr.

(57) ABSTRACT

Devices are provided for inhibiting the electrical activity of an excitable cell through the application of a pulse of light which includes a substrate and a photoreactive film both of non-conducting material and laid directly on one another, in which the photoreactive film includes a layer of semiconductor polymer material and has an interface surface which can be placed in contact with an excitable cell and an electrolyte solution. After absorbing light, when placed in contact with the excitable cell and the electrolyte solution, the photoreactive film produces a potential difference across this interface surface which is capable of giving rise to hyperpolarization of the membrane of the excitable cell. Methods of inhibiting the electrical activity of excitable cells using such devices are also provided.

4 Claims, 1 Drawing Sheet

(51) Int. Cl.
C09D 165/00 (2006.01)
C08G 61/12 (2006.01)

(52) U.S. Cl.
CPC ... C08G 61/126 (2013.01); C08G 2261/3223 (2013.01); C08J 2300/16 (2013.01); C08J 2465/00 (2013.01)

(56) References Cited

OTHER PUBLICATIONS

Diego Ghezzi, Maria Rosa Antognazza, Rita Maccarone, Sebastiano Bellani, Erica Lanzarini, Nicola Martino, Maurizio Mete, Grazia Pertile, Silvia Bisti, Guglielmo Lanzani and Fabio Benfenati, A polymer optoelectronic interface restores light sensitivity in blind rat retinas, Nature Photonics, May 2013, pp. 400-406, vol. 7, www.nature.com/naturephotonics, DOI:10.1038/NPHOTON.2013.34, Italy.

Harald Janovjak, Stephanie Szobota, Claire Vvyart, Dirk Trauner and Ehud Y. Isacoff, A light-gated, potassium-selective glutamate receptor for the optical inhibition of neuronal firing, HHS Public Access, Author manuscript, Nat Neurosci, Feb. 2001, pp. 1-19, vol. 13(8): 1027-1032. doi: 10.1038/nn.2589.

Jeanne T Paz, Thomas J Davidson, Eric S Frechette, Bruno Delord, Isabel Parada, Kathy Peng, Karl Deisseroth and John R Huguenard, Closed-loop optogenetic control of thalamus as a tool for interrupting seizures after cortical injury, Nature Neuroscience, Jan. 2013, pp. 64-73, vol. 16, No. 1, Nature America Inc., doi:10.1038/nn.3269.

Jan TØnnesen, Andreas T. SØrensen, Karl Deisseroth, Cecilia Lundberg and Merab Kokaia, Optogenetic control of epileptiform activity, Pnas, Jul. 21, 2009, pp. 12162-12167, vol. 106, No. 29, www.pnas.org/cgi/doi/10.1073/pnas.0901915106, Sweden.

M.R. Antognazza, D. Ghezzi, D. Musitelli, M. Garbugli and G. Lanzani, A hybrid solid-liquid polymer photodiode for the bioenvironment, Applied Physics Letters 94, 2009, 243501-1, American Institute of Physics [DOI: 10.1063/1.3153846].

Volker Busskamp, Jens Duebel, David Balya, Mathias Fradot, Tim James Viney, Sandra Siegert, Anna C. Groner, Erik Cabuy, Valérie Forster, Mathias Seeliger, Martin Biel, Peter Humphries, Michel Paques, Saddek Mohand-Said, Didier Trono, Karl Deisseroth, José A. Sahel, Serge Picaud, Botond Roska, Genetic Reactivation of Cone Photoreceptors Restores Visual Responses in Retinitis Pigmentosa, Science, Jul. 23, 2010, pp. 413-418, vol. 329, www.sciencemag.org, USA.

Xue Han, Edward S. Boyden, Multiple-Color Optical Activation, Silencing, and Desynchronization of Neural Activity, with Single-Spike Temporal Resolution, Plos One, Mar. 2007, Issue 3, www.plosone.org, e299, USA.

Diego Ghezzi, Maria Rosa Antognazza, Marco Dal Maschio, Erica Lanzarini, Fabio Benfenati & Guglielmo Lanzani, A Hybrid bioorganic interface for neuronal photoactivation, Nature Communications, Jan. 18, 2011, pp. 1-7, 2:166, DOI:10.1038/ncomms1164, www.nature.com/naturecommunications, Italy.

Stergios Logothetidis, Despoina Georgiou, Argiris Laskarakis, Christos Koidis, Nikolaos Kalfagiannis, In-line spectroscopic ellipsometry for the monitoring of the optical properties and quality of roll-to-roll printed nanolayers for organic photovoltaics, Solar Energy Materials & Solar Cells 112, 2013, pp. 144-156, www.elsevier.com/locate/solmat, Elsevier, Greece.

\* cited by examiner

ORGANIC DEVICES FOR THE PHOTOINHIBITION OF EXCITABLE CELLS

CROSS-REFERENCE TO RELATED APPLICATIONS

This application is a National Phase Application of PCT International Application No. PCT/IB2014/063616, International Filing Date, Aug. 1, 2014, claiming priority to Italian Patent Application No. TO2013 A000665 (102013902181715), filed Aug. 2, 2013, each of which is hereby incorporated by reference in its entirety.

FIELD OF THE INVENTION

This invention relates to a device for the photoinhibition of excitable cells (for example, cell cultures, brain sections, retinal explants and sections, muscle cells, cardiomyocytes, etc.) through hyperpolarisation of the membrane potential of the cells placed in contact with the device.

BACKGROUND OF THE INVENTION

It is known from the state of the art that it is possible to bring about photo-hyperpolarisation of the membrane potential, in particular of nerve cells. In particular the publications: Janovjak, Harald; Szobota, Stephanie; Wyart, Claire; Trauner, Dirk; Isacoff, Ehud Y (2010), "A light-gated, potassium-selective glutamate receptor for the optical inhibition of neuronal firing". Nat. Neurosci. 13: 1027-1032 and WO 2010/051343 report hyperpolarisation of the membrane potential and inhibition of the electrical activity of a genetically modified neurone through the use of photosensitive proteins expressed in the cell through viral infection, which can be activated following a light-induced conformational change.

In addition to this the publications: Han, Xue; Boyden, Edward S. (2007) "Multiple-color optical activation, silencing, and desynchronization of neural activity, with single-spike temporal resolution". PloS One 2: e299 and US 2011/301,529 report hyperpolarisation of the membrane potential and inhibition of the electrical activity of a cell through the use of light-sensitive ion pumps of microbial original (microbial rhodopsin) expressed in the cell through viral infection.

Similar hyperpolarisation techniques have been used in the cure of degenerative diseases of the retina (Busskamp, Volker; Duebel, Jens; Balya, David; Fradot, Mathias; Viney, Tim J; Siegert, Sandra; Groner, Anna C; Cabuy, Erik; Forster, Valérie; Seeliger, Mathias; Biel, Martin; Humphries, Peter; Paques, Michel; Mohand-Said, Saddek; Trono, Didier; Deisseroth, Karl; Sahel, José A; Picaud, Serge; Roska, Botond (2010) Genetic reactivation of cone photoreceptors restores visual responses in retinitis pigmentosa. Science 329: 413-417; Polosukhina, Aleksandra; Litt, Jeffrey; Tochitsky, Ivan; Nemargut, Joseph; Sychev, Yivgeny; De Kouchkovsky, Ivan; Huang, Tracy; Borges, Katharine; Trauner, Dirk; Van Gelder, Russell N; Kramer, Richard H (2012) Photochemical restoration of visual responses in blind mice. Neurone. 2012 75(2):271-82) and focal epilepsy (Tønnesen, J., Sørensen, A. T., Deisseroth, K., Lundberg, C. & Kokaia, M. (2009) Optogenetic control of epileptiform activity. Proc. Natl. Acad. Sci. USA 106: 12162-12167. Paz, Jeanne T; Davidson, Thomas J; Frechette, Eric S; Delord, Bruno; Parada, Isabel; Peng, Kathy; Deisseroth, Karl; Huguenard, John R. (2013) Closed-loop optogenetic control of thalamus as a tool for interrupting seizures after cortical injury. Nat. Neurosci. 16: 64-70) exclusively in experimental animals.

These strategies presuppose genetic expression of light-sensitive heterologous proteins in the cell through viral constructs. At the present time it is still not possible to photoinhibit excitable cells without genetically modifying the target cells. These strategies have unavoidable collateral effects. In fact the viral vectors are potentially toxic, give rise to inflammatory reactions in the host tissue, and cause expression of a magnitude and duration which can vary over time. In addition to this the heterologous protein can interfere with cell functions and give rise to functional abnormalities.

It is known from previous publications by the inventors that a device comprising a glass substrate, an anode contact, a semiconductor polymer and electrolyte means is capable of giving rise to depolarisation of the membrane potential of excitable cells placed above the polymer surface. This depolarisation gives rise to photoexcitation similar to that which can be obtained through electrical stimulation [M. R. Antognazza, D. Ghezzi, D. Musitelli, M. Garbugli and G. Lanzani (2009) A hybrid solid-liquid polymer photodiode for the bioenvironment. Appl. Phys. Lett. 94: 243501; D. Ghezzi, M. R. Antognazza, M. Dal Maschio, E. Lanzarini, F. Benfenati and G. Lanzani (2011) A hybrid bioorganic interface for neuronal photoactivation. Nat. Commun. 2: 166; D. Ghezzi, M. R. Antognazza, R. Maccarone, S. Bellani, E. Lanzarini, N. Martino, M. Mete, G. Pertile, S. Bisti, G. Lanzani and F. Benfenati (2013) A polymer-based interface restores light sensitivity in rat blind retinas. Nat. Phot. 7: 400-406].

The inventors have surprisingly found that by layering a photo-sensitive polymer directly onto a substrate of non-conducting material a device is obtained which produces a potential difference across the contact surface with the cell, when subjected to a pulse of light radiation, such as to induce hyperpolarisation of the membrane of the excitable cell, thus obtaining an effect which is the opposite of that in the known device.

SUMMARY OF THE INVENTION

One object of the invention therefore constitutes a device for inhibiting the electrical activity of an excitable cell through the application of a pulse of light, consisting of a substrate of an electrically insulating material and a photoreactive film laid directly upon one other, the said photoreactive film including a layer of semiconductor polymer material and having an interface surface which can be placed in contact with an excitable cell and an electrolyte solution, in which the photoreactive film, when placed in contact with the excitable cell and electrolyte solution, produces a potential difference across the interface surface after absorbing light, this difference being capable of inducing hyperpolarisation of the membrane of the excitable cell.

Another object of the invention is to provide a device for the photoinhibition of electrical activity in an excitable cell which is capable of overcoming the disadvantages of known devices.

Further features and advantages of devices according to the invention will be apparent from the following detailed description referring to the attached drawings.

DETAILED DESCRIPTION

Figure 1:
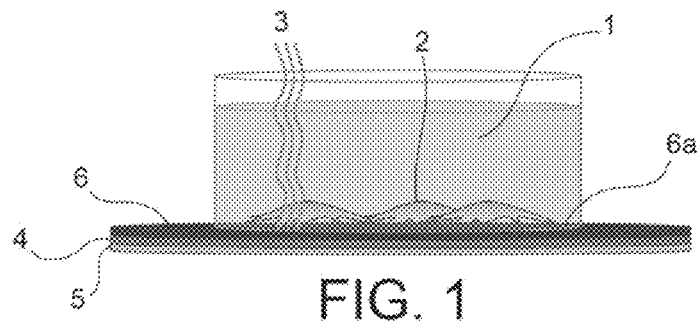
FIG. 1 shows a diagram of a device according to the invention with a neurone culture grown on an interface surface of the device.

FIG. 1 illustrates diagrammatically a device according to the invention in an experimental configuration for applications in vitro, in which a culture of excitable cells 2, immersed in an electrolyte solution 1, is caused to grow on the device. For the purposes of this invention, by excitable cell is conventionally meant a cell capable of providing an active electrical response (i.e. excitation of the membrane) following the application of an external electrical stimulus when that stimulus exceeds a threshold potential for the membrane. Excitable cells are, for example, nerve cells and muscle cells.

In particular it will be seen in FIG. 1 that the device according to the invention consists of a photoreactive film comprising several layers 4, 6 and supported by a planar substrate of insulating material 5. All the layers of the photoreactive film and the substrate are therefore in general made of non-conducting material.

The photoreactive film has an interface surface 6a in contact with excitable cells 2 and the electrolyte solution (or electrolyte medium) 1, and comprises a semiconductor polymer material 4 which in the example illustrated is covered by a dielectric layer 6 (which in this case therefore provides the abovementioned interface surface).

The device according to this invention is capable of generating an electrochemical stimulus within electrolyte medium 1 in the vicinity of at least one excitable cell 2 through the absorption of a light stimulus 3 by semiconductor polymer material 4. This electrochemical stimulus takes the form of a potential difference across interface surface 6a which is capable of giving rise to hyperpolarisation of the membrane of excitable cell 2. For the purposes of this invention, by hyperpolarisation is meant a condition in which the potential difference between the inside and the outside of the cell membrane increases with respect to the reference condition.

As mentioned above, the device illustrated in the figures is configured for application in vitro. It is however possible to conceive of in vivo applications, in particular an implant in which the photoreactive film, which may be supported by a substrate, forms part of an implantable device in an animal body. In an application of this kind, contact with the excitable cells is brought about by positioning the implant in contact with the tissue in question, while the electrolyte solution needed for functioning of the device comprises the body fluids themselves.

For in vitro applications, substrate 5 may be transparent (for example glass) in order to allow illumination from beneath, or semi-transparent (for example, cellulose, silicone, silk fibroin, polymer materials such as poly(lactic-co-glycolic) acid or PLGA, polyglycolic acid or PGA, polycaprolactone or PCL, polymethylmethacrylate or PMMA) in the case of illumination from above. In in vivo applications this substrate 5 must be flexible, biocompatible and partly absorbable, such as for example cellulose, PCL or fibroin.

Silk fibroin may be regenerated using a variety of protocols. Among these, the thin compact fibroin films obtained by solvent casting offer the highest level of biocompatibility, transparency, possibility of accurately monitoring the biodegradation process and self-adhesive properties. These films have therefore been used to produce devices intended for use in vivo, in particular in subretinal prostheses.

Suitable purification, extraction and deposition protocols have been developed for this purpose. The process starts with fresh cocoons. The fibres are purified by treating the outer coating of the cocoon with hot water in order to remove the protein sericin. The fibres purified in this way are converted into a thin film by: (i) dissolution in aqueous solutions of 9M lithium bromide; (ii) dialysis or ultrafiltration to produce an aqueous solution; (iii) deposition of the thin film at ambient temperature under controlled conditions in terms of temperature, humidity and circulation of air; (iv) suitable heat treatment of the thin film to obtain the desired mechanical and elastic properties, environmental stability and biodegradability.

Poly (lactic-co-glycolic) acid or PLGA is a co-polymer whose biodegradability and biocompatibility properties are well known. The material has in fact been approved by the Food and Drug Administration (FDA) for therapeutic purposes, for the release of drugs and as a biomaterial for in vivo applications. The degradation time can be varied, depending upon the process parameters used. The elastic properties, thickness and homogeneity of the substrate can be optimised through a suitable choice of solvent, (chlorinated solvents, TFH, acetone, ethyl acetate), the deposition technique (spin-coating, casting, doctor blading) and the parameters relating thereto, the temperature and the duration of the post-processing thermal processes.

In a similar way to the above material, polymethylmethacrylate (PMMA) and polycaprolactone (PCL) are polymers which lend themselves to deposition in the form of a thin film, up to a few μm in thickness, with optimally uniform properties. Unlike PMMA, PCL is biodegradable and is therefore suitable for use in vivo. PMMA has the advantage that it has a higher softening temperature (160° C. in comparison with 60° C.) and is therefore more compatible with post-processing thermal processes.

Other types of polymer are suitable for the proposed applications, both in vitro and in vivo, for example, parylene-C, various types of polyesters and polypropylene. Again in these cases it is possible to obtain thin films of controlled thickness, of up to a few µm.

The technique typically used to obtain thin films of the order of µm is deposition on a supporting glass substrate. This makes it possible to obtain optimum homogeneity and flatness properties, and to perform all the subsequent operations of fabrication of the device (deposition of the active material, heat treatments, provision of holes through laser micromachining techniques) in a repeatable way. At the end of the process the entire device can be removed from the supporting substrate without damage.

All the abovementioned materials are suitable for processing through laser micromachining.

Devices intended for use in vivo, in particular for retinal implants, are obtained from larger devices by means of a laser cutting technique.

A laser of suitable wavelength (preferably 515 nm or in any event within the optical absorption window for the active material) is focused on the sample. A suitable movement system makes it possible to accurately control the position of the sample with respect to the laser beam in the three X, Y and Z directions. A control program also makes it possible to obtain the shape of implant desired. A specific device required by the surgical implantation technique provides for the manufacture of trapezoidal shapes, which are more suitable for the insertion procedure, and the production of an asymmetrical recognition mark which makes it possible to distinguish the front surface of the device from the back surface in the course of a surgical procedure.

The technique makes it possible to optimise the dimensions of the devices suitably and extremely accurately on the basis of the dimensions of the animal's retina, to achieve excellent repeatability in manufacture of the device, and to avoid a sharp edge, which would irremediably damage retinal tissue. Conversely the edges of the device obtained in this way are smoothed off and minimally invasive.

Devices intended for implants are suitably perforated to allow the exchange of nutrients and oxygenation of the underlying retinal tissues. The diameter of the holes varies within the range 1-5 µm, and the distance between one hole and another can be varied continuously in the range 10-100 µm.

With regard to semiconductor polymer material 4 (which has a thickness of between 50 and 1000 nm, preferably between 150 and 300 nm), this is generally an intrinsic semiconductor with wide bandgap (of between 1 and 2 eV), much greater than the thermal energy at body temperature (approximately 0.027 eV) and having electrical conductivity of an order of magnitude which is less than or equal to $10^{-5}$ S/m and mobility of the charge carriers of an order of magnitude less than or equal to $10^{-4}$ cm$^2$V/s at ambient temperature. The semiconductor polymer material may possibly be doped with an electron acceptor, preferably in relative concentrations between 0.5:1 and 3:1 with respect to the semiconductor polymer. Preferably, the semiconductor polymer material is poly(3-hexylthiophene-2,5-diyl) regioregular (P3HT). Other suitable polymers are by way of example but not exhaustively poly(3-octylthiophene) (P3OT), poly[2-methoxy-5-(2'-ethylhexyloxy)-p-phenylenevinylene] (MEH-PPV), poly[2-methoxy-5-(3',7'-dimethyloctyloxy)-1,4-phenylenevinylene] (MDMO-PPV), poly[2,6-(4,4-bis-(2-ethylhexyl)-4H-cyclopenta[2,1-b;3,4-b']-dithiophene)-alt-4,7-(2,1,3-benzothiadiazole)] (PCPDTBT).

In general all the semiconductor polymers used in organic electronics may be used in the device. Materials which are suitable as electron acceptors are phenyl-C61-butyric-acid-methyl ester (PCBM) or other fullerenes and their derivatives (ICBA; ICMA), for example C60 and C70 or other acceptors of a polymer nature, for example, N2200, or low molecular weight molecules used in organic photovoltaic cells.

The semiconductor polymer material is deposited in the selected substrate in the form of a thin film from a solution in organic solvent. Where an electron acceptor material is used the relative concentration of the latter with respect to the material used as electron donor is suitably calibrated on the basis of the interface potential which it is desired to obtain; typical values are within the range (0.5:1)-(3:1). The parameters for deposition by spin coating (duration of the entire process, rotation speed and acceleration, number and duration of ramps) are optimised on the basis of the properties of the solution to be deposited and of the different hydrophilicity degree of the substrate.

Dielectric layer 6 (having a thickness preferably between 10 and 100 nm, even more preferably between 20 and 50 nm), which covers the surface of the organic polymer, comprises a thin compact layer of oxides. The deposition technique must be compatible with the underlying polymer and must allow for the manufacture of a sufficiently compact thin layer. Selection of the material depends on biocompatibility properties, transparency to visible light in the case of illumination from above, and the dielectric constant, in order to optimise coupling with the electrolyte medium. Deposition techniques are characterised by the possibility of working at ambient temperature (avoiding damaging the active material and the substrate), accurately controlling the thickness of the insulating layer, and forming an extremely thin film which is at the same time perfectly compact. Examples of possible materials include: silicon carbide SiC, titanium carbide TiC, silicon nitride $Si_3N_4$, titanium dioxide $TiO_2$, silicon dioxide $SiO_2$, aluminium oxide $Al_2O_3$, tantalum oxide $Ta_2O_5$ and zirconium oxide ZrO. The chosen deposition technique takes place using pulsed laser light, or in ultra-high vacuum UHV, or with suitable pressures of deposition gas, such as oxygen and argon.

Electrolyte medium 1 comprises an isotonic aqueous solution of ions capable of keeping the excitable cells alive (for example, phosphate-buffered saline, Ame's medium, minimum essential medium, Neurobasal medium, Krebs-Ringer solution, artificial cerebrospinal fluid, etc.) in contact with oxide film 6.

The mechanism of action of the device described above is radically distinct from both the effect of inhibiting bacterial opsins and the photoexcitation mechanism previously published by the inventors. When irradiated by light radiation in the visible spectrum the device intercepts the photons striking the polymer layer (conversion mechanism); the charge transfer which this produces initiates hyperpolarisation of the cell membrane.

In the present device light strikes the surface of the polymer from the bottom or top, passing through the substrate or the electrolyte medium and the dielectric layer respectively, without in any case undergoing appreciable absorption or giving rise to scattering phenomena. Preparation of the polymer solution and the subsequent procedure for deposition of the photosensitive film takes place preferably in ambient atmosphere. Exposure to atmospheric oxygen gives rise to significant p-type doping phenomena in the device, which modifies the photophysics of the organic semiconductor in relation to the native film. These doping processes may also be further encouraged by surface treatment processes (oxygen plasma), sterilisation in ethylene oxide, deposition of the oxide using low pressure oxygen as the reaction medium. Light absorption in native polymers gives rise to a small portion of pairs of ions of opposite charge called polaron pairs, which are weakly linked by Coulomb forces (electrostatic attraction). A polaron may be regarded as a charge carrier which is almost free to move, or has low mobility between $10^{-4}$ and $10^{-8}$ cm²V/s within the polymer film. The oxygen present in the polymer film acts as a trap for the negative polarons and as a site for dissociation for the neutral state, as described below:

$$P + h\upsilon + O_2 = P^* + O_2 = (P^+ + O_2^-)$$

$$PP + h\upsilon + O_2 = P^+ + P^- + O_2 = P + (P^+ + O_2^-)$$

where P is the neutral polymer segment, $P^+$ and $P^-$ represent the positive and negative polarons respectively on the polymer surface, and $P^*$ represents the excited neutral polymer.

As a consequence, in semiconductor polymers which have been heavily doped with oxygen the absorbed photons give rise to almost free positive charges and immobilised negative charges, with a quantum efficiency of virtual unity.

Under illumination the device develops a potential difference across its thickness, as a result of a combination of processes of charge separation and diffusion and electrical drift, thus behaving like a condenser. Consequently an intense localised electrical field is generated on the surface of the polymer, which aids charge separation. This electrical field and the condenser structure are preserved by a protective dielectric layer 6, comprising a compact material having high k. Because the capacity of a flat parallel plate condenser is given by $C = (k * \in_0 * A)/t$, where A is the area of the condenser, k is the relative dielectric constant of the medium, $\in_0$ is the dielectric permittivity of vacuum and t is the thickness of the oxide layer, the materials of choice are materials having a high dielectric constant, preferably $Al_2O_3$ (k=10), $ZrO_2$ (k=25) and $Ta_2O_5$ (k=20-40), and thicknesses of the order of 20 nm.

The charge dislocation generated at the surface of the photosensitive polymer resulting from the illumination, which is preserved by the dielectric, influences and modifies the external ionic environment causing a rearrangement of the ions in the electrolyte solution in contact with the device. The new ion distribution changes the membrane potential, increasing the excess positive charge density on its outer surface and therefore increasing the potential difference between the inside and outside of the membrane $(V_m)$ generating hyperpolarisation.

If insulating oxide layer 6 is omitted from the structure of the device, when calculating the capacity of the layer of accumulated charge only the dielectric constant of the photosensitive polymer, which in most cases is equal to 3-4, has to be taken into account. The presence of the oxide layer is therefore important, not only guaranteeing adequate protection for the semiconductor material but also suitably bringing about capacitive coupling with the electrolyte medium.

This invention differs substantially from the device previously used for the depolarisation of neurone cultures in vitro, characterised by the presence of an anode contact between the substrate and the photosensitive material. In fact the inclusion of an electrical contact in the structure of the device gives rise to a substantial change in the interface energy levels and a completely different method of functioning. In the presence of ITO (which has a conductivity of more than $10^4$ S/m) or another conducting material these behave as electrical charge acceptors and charge transfer processes at the interface become the predominant mechanisms, in contrast with the case in which the photosensitive material is deposited on the insulating material. This gives rise to an imbalance in the distributor charge within the photosensitive polymer which has accumulated at the interface with the electrolyte, and therefore a different (depolarisation) effect on the biological tissue.

Figure 2:
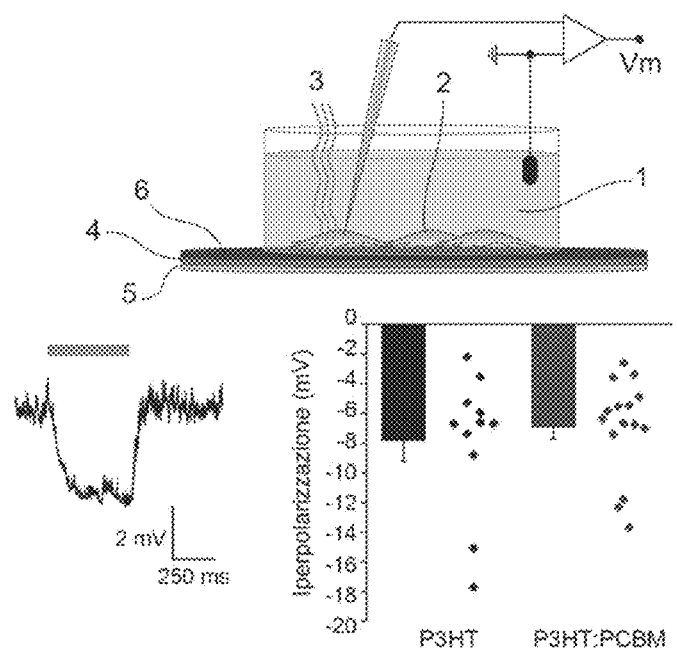
FIG. 2 shows: (a) A diagram of the device in FIG. 1, arranged for patch-clamp recording. (b) An example of an electrophysiological recording of the membrane potential in an in-vitro hippocampus neurone in which the hyperpolarisation was measured using the patch-clamp technique in a current-clamp configuration. A glass pipette is used to measure changes in potential of the neurone membrane adhering above the polymer and immersed in the extracellular liquid. The light stimulus (horizontal grey bar) gives rise to a significant increase in the internal electronegativity of the cell membrane (hyperpolarisation of the membrane potential, black line). (c) Absolute values (individual values and means±standard errors of the mean) for the hyperpolarisation induced by light in mV recorded in neurones grown on P3HT (11 neurones) or on a P3HT and PCBM mixture (15 neurones). No significant difference was found between the two experimental samples.

A device to which this invention relates is therefore capable of giving rise to hyperpolarisation of the cell membrane potential $(V_m)$. In the case of an excitable cell like a neurone this effect is capable of reproducing the effects of endogenous inhibition brought about by the action of GABAergic interneurones and preventing propagated electrical activity (firing of action potentials) in the cell in contact with the device. This effect is described in FIG. 2 in the case of an in vitro hippocampus neurone.

Figure 3:
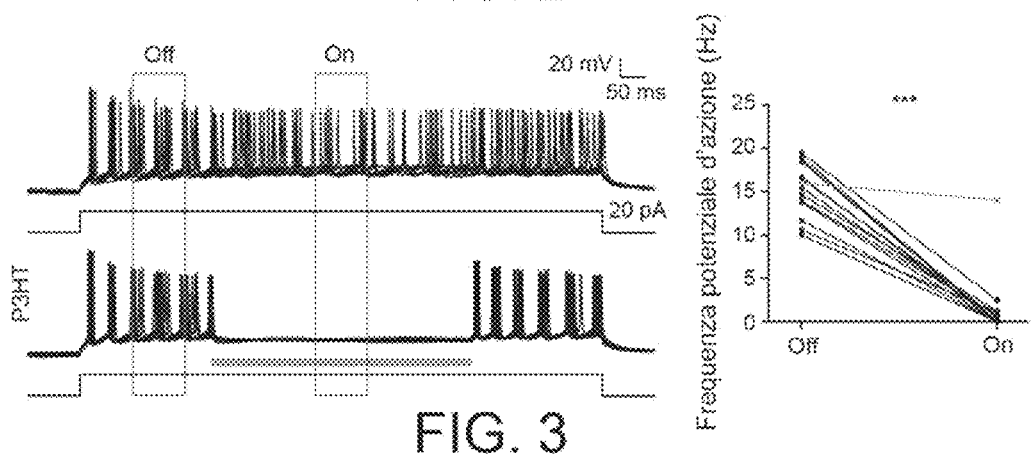
FIG. 3 shows: (a) Recordings from a neurone grown on standard substrate (glass; top line) or on the P3HT device (bottom line) stimulated through the input of 20 pA of current by patch-clamp in a "current-clamp" configuration. Both the neurones respond to the input of current with depolarisation of the membrane potential, exceeding the threshold and giving rise to the discharge of high frequency action potentials (spikes). The light stimulus (horizontal bar) causes almost total silencing of "firing" activity exclusively in the neurone grown on the device. (b) The effect of light on the frequency of the discharge of action potentials in Hertz (1 Hz=1 action potential/second) in a population of hippocampus neurones in culture (each pair of symbols connected by a line represents the response of an individual neurone to light in the absence, "off", or presence, "on", of the light stimulus). The discharge frequency was measured for the various cells during the time intervals indicated by the squares in the panel corresponding to the "light off" and "light on" conditions. The asterisks show that on the basis of the statistical analysis performed (Student's t test) the effect is highly significant.

Membrane hyperpolarisation induced by the device, which is the subject matter of this invention, is capable of inhibiting the electrical activity of an excitable cell, as described in FIG. 3 in the case of a hippocampus neurone.

In excitable cells hyperpolarisation moves the membrane potential away from the threshold potential, unleashing the action potential and therefore has an inhibitory action on the electrical activity propagated by the neurone. In addition to this, in all cells which do not express an action potential but release chemical messages like neurotransmitters or hormones, hyperpolarisation inhibits secretory activity as a consequence of depolarisation of their membrane potential (for example, photoreceptors, bipolar cells of the retina, or neurosensory cells in the cochlea and vestibular system).

The invention claimed is:

1. A device for inhibiting electrical activity of an excitable cell by application of a light pulse, comprising a substrate of electrically insulating material and a photoreactive film layered directly on one another, the photoreactive film comprising a layer of semiconducting polymer material and having an interface surface which can be placed in contact with an excitable cell and an electrolyte solution, in which the photoreactive film, when contacted with the said excitable cell and electrolyte solution, produces a potential difference across the interface surface which will induce hyperpolarisation of the membrane of said excitable cell after absorbing light, wherein the photoreactive film further comprises a layer of dielectric material placed on the layer of semiconducting polymer material.

2. The device of claim 1, wherein the substrate comprises material transparent to light radiation within the absorption window for the semiconducting polymer material.

3. The device of claim 1, wherein the substrate comprises a flexible, biocompatible material which can be partly absorbed in animal or human tissue.

4. The device of claim 1, wherein the photoreactive film and substrate comprise an array of through-holes of a diameter between 1 and 5 μm mutually spaced at a distance of between 10 and 100 μm.

* * * * *